US009265526B1

(12) United States Patent
Abdou

(10) Patent No.: US 9,265,526 B1
(45) Date of Patent: Feb. 23, 2016

(54) VARIABLE-SHAPED, EXPANDABLE DEVICE AND METHOD FOR MINIMALLY-INVASIVE USE

(76) Inventor: Samy Abdou, San Diego, CA (US)

( * ) Notice: Subject to any disclaimer, the term of this patent is extended or adjusted under 35 U.S.C. 154(b) by 391 days.

(21) Appl. No.: 13/073,860

(22) Filed: Mar. 28, 2011

Related U.S. Application Data

(60) Provisional application No. 61/341,089, filed on Mar. 27, 2010.

(51) Int. Cl.
A61B 1/32 (2006.01)
A61B 17/34 (2006.01)

(52) U.S. Cl.
CPC ............... A61B 17/3439 (2013.01); A61B 1/32 (2013.01)

(58) Field of Classification Search
CPC ........... A61B 2017/00566; A61B 1/32; A61B 17/02; A61B 17/0218; A61B 17/3421; A61B 17/3423; A61B 17/3431; A61B 17/3439; A61B 2017/0225; A61B 17/3425; A61B 17/3429; A61B 17/3433; A61B 17/3445
USPC .............. 604/96.01, 101.02, 103.02; 138/93, 138/118–120
See application file for complete search history.

(56) References Cited

U.S. PATENT DOCUMENTS

| | | | | |
|---|---|---|---|---|
| 3,260,412 A | * | 7/1966 | Larkin | 222/107 |
| 5,545,179 A | * | 8/1996 | Williamson, IV | 606/213 |
| 5,795,289 A | * | 8/1998 | Wyttenbach | 600/207 |
| 5,967,970 A | * | 10/1999 | Cowan et al. | 600/207 |
| 6,360,750 B1 | * | 3/2002 | Gerber et al. | 128/898 |
| 8,192,358 B2 | * | 6/2012 | Leahy | 600/207 |
| RE44,380 E | * | 7/2013 | de la Torre et al. | 604/256 |
| 8,491,471 B2 | * | 7/2013 | Deshmukh et al. | 600/206 |
| 2003/0014068 A1 | * | 1/2003 | Bonutti et al. | 606/190 |
| 2006/0287583 A1 | * | 12/2006 | Mangiardi | 600/208 |
| 2008/0081951 A1 | * | 4/2008 | Frasier et al. | 600/207 |
| 2008/0086080 A1 | * | 4/2008 | Mastri et al. | 604/95.03 |
| 2010/0286483 A1 | * | 11/2010 | Bettuchi et al. | 600/207 |
| 2011/0118552 A1 | * | 5/2011 | Fischvogt | 600/206 |
| 2012/0190933 A1 | * | 7/2012 | Kleyman | 600/207 |
| 2012/0238825 A1 | * | 9/2012 | Smith | 600/207 |
| 2012/0245425 A1 | * | 9/2012 | Okoniewski | 600/207 |
| 2013/0190573 A1 | * | 7/2013 | Smith | 600/207 |

OTHER PUBLICATIONS http://liquidmetal.com/our-products/product-parts/, What we Sell, 5 pages, downloaded from the internet Mar. 27, 2014.
(Continued)

Primary Examiner — Christian Sevilla
Assistant Examiner — Eric S Gibson
(74) Attorney, Agent, or Firm — Gazdzinski & Associates, PC

(57) ABSTRACT

Disclosed herein are devices and systems adapted to position within a subject and methods of use therewith. The device includes a conduit body having at least a first layer and a second opposable layer manufactured from a biocompatible and malleable material that permits safe positioning within the subject. The device also includes an enclosed intervening cavity positioned between the first and second layers, the first surface of the first layer having at least one feature configured to interlock with the second surface of the second layer. The conduit body is configured to transition from a first state to a second state upon application of a suction force to the intervening cavity wherein the conduit body is less rigid in the first state than when the conduit body is in the second state, and wherein the conduit body is adapted to remain in the second state after removal of the suction force.

40 Claims, 8 Drawing Sheets

(56) References Cited

OTHER PUBLICATIONS https://www.brainlab.com/surgery-products/overview-platform-products/curve-image-guided-surgery, Curve, The Ultimate Control and Information Center; 8 pages, downloaded from the internet Mar. 27, 2014.

"Frameless Stereotaxy of the Brain" by Mcinerney and Roberts in *Mt Sinai J Med.* Sep.; 67(4):300-10.
"Devices for Targeting the needle" by Barbre in *Neurosurg Clin N. Am.* Apr. 2009; 20(2): 187-91.

* cited by examiner

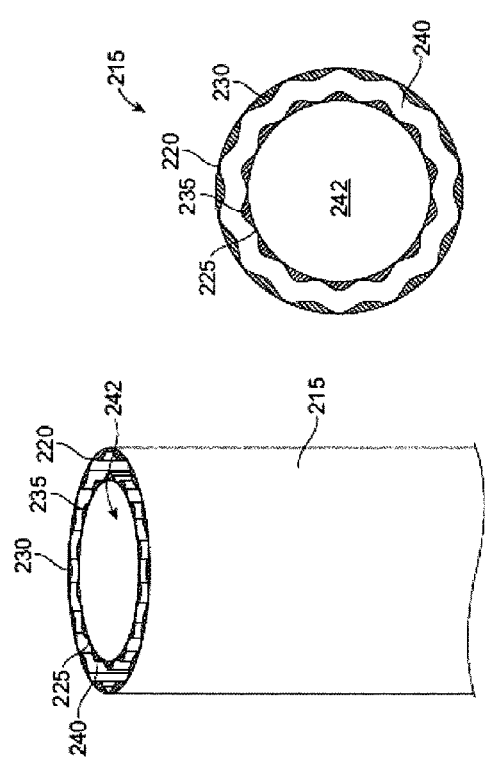
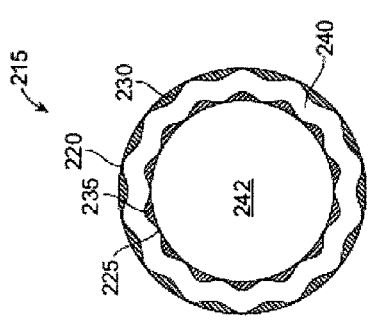
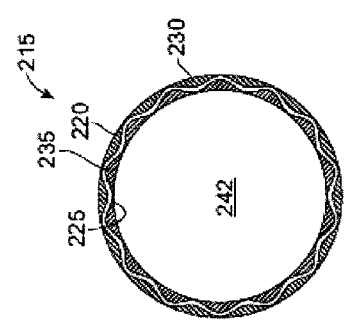
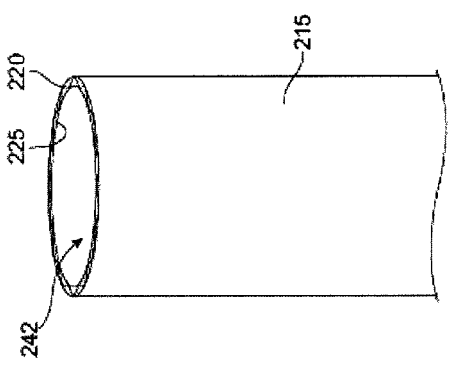
FIG. 2A
FIG. 2B
FIG. 2C
FIG. 2D

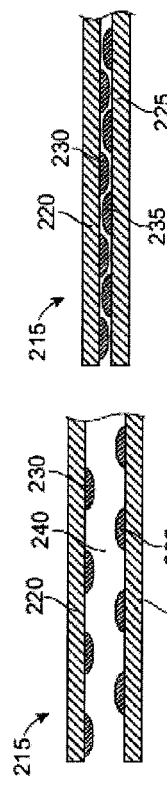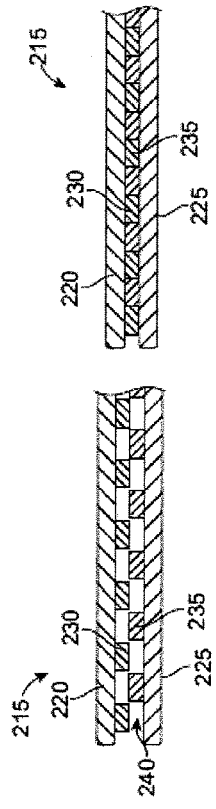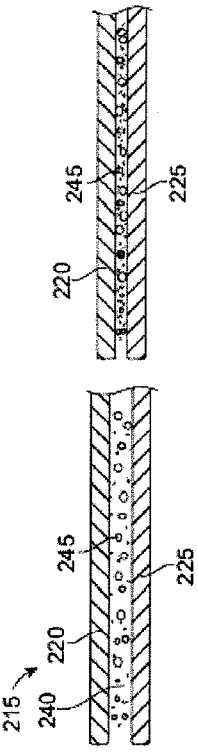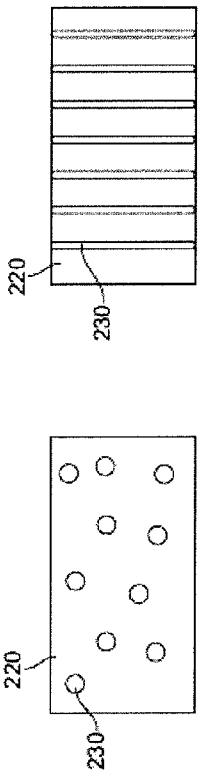

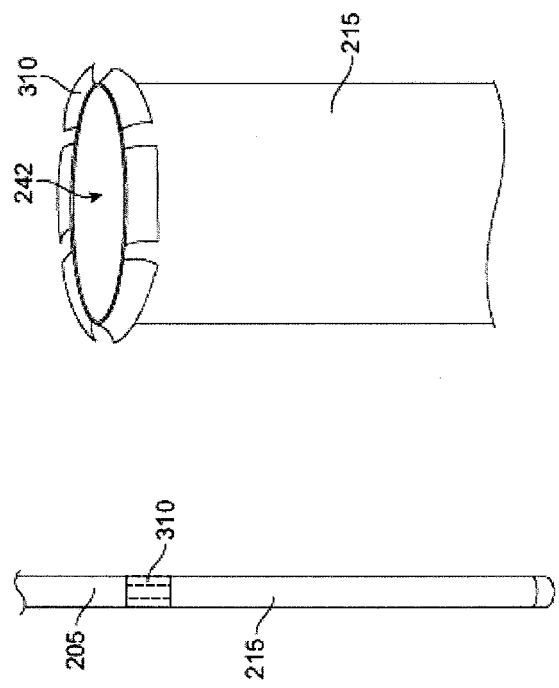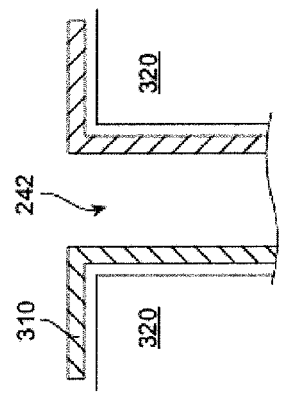
FIG. 9B
FIG. 9C
FIG. 9A

VARIABLE-SHAPED, EXPANDABLE DEVICE AND METHOD FOR MINIMALLY-INVASIVE USE

REFERENCE TO PRIORITY DOCUMENTS

This application claims the benefit of priority to U.S. Provisional Patent Application Ser. No. 61/341,089, filed on Mar. 27, 2010. Priority of the filing date and the disclosure of the Provisional Patent Application is hereby incorporated by reference in its entirety.

BACKGROUND

The present disclosure is directed to minimally-invasive devices that are used to retract tissues and to form a working channel for surgical procedures.

Surgery involves a complex set of manual tasks with numerous limitations, such as a surgeon's vision, manual dexterity and the risk of tissue damage. Minimally-invasive techniques and improved visualization and illumination for minimally-invasive procedures have improved the success rate of such surgeries. Conventional retractor systems used in surgery have numerous limitations. Conventional retractors are generally made of rigid materials and are generally fixed in length and width. They are prone to cause damage of adjacent tissues either by excessive retraction or blunt trauma when pressed against delicate tissues. Further, rigid retractors do not conform well to the surrounding tissue. Endoscopic instruments have limited utility, particularly when they are used in neurosurgical procedures. Currently available designs limit the working channel diameter. This prevents the surgeon from performing surgery with anything other than probe-like instruments.

SUMMARY

In view of the proceeding, there is a need for an improved tissue retractor for minimally-invasive procedures. In particular, there is a need for a tissue retractor that can be inserted in a minimally-invasive manner to form and retain a tissue corridor for performing surgery that effectively conforms to the tissue and avoids damaging surrounding tissues. Further, the retractor can reversibly transition from a first state to a second state, wherein it is in a more malleable state when in the first state and it is in a more rigid state when in the second state.

In one aspect, disclosed herein is a device adapted to position within a subject. The device includes a conduit body having at least a first layer and a second opposable layer. The first and second layers are manufactured from a biocompatible and malleable material that permits safe positioning within the subject. The device also includes an enclosed intervening cavity positioned between the first and second layers. The first surface of the first layer forms a first perimeter of the intervening cavity and a second surface of the second layer forms a second perimeter of the intervening cavity. The first surface of the first layer comprises at least one feature configured to interlock with the second surface of the second layer. The conduit body is configured to transition from a first state to a second state upon application of a suction force to the intervening cavity wherein the conduit body is less rigid in the first state than when the conduit body is in the second state, and wherein the conduit body is adapted to remain in the second state after removal of the suction force.

The conduit body of the device can be configured to create a surgical conduit within a body of the subject. The at least one feature of the first surface of the first layer can interlock with the second layer when the conduit body is in the second state. A volume of the intervening cavity can be greater when the conduit body is in the first state than when the conduit body is in the second state. The at least one feature of the first surface of the first layer can be separated a distance from the second layer when the conduit body is in the first state. The distance the first layer and the second layer are separated can be greater when the conduit body is in the first state than when the conduit body is in the second state. The conduit body can have a cylindrical configuration. The conduit body can surround an internal central cavity. The central cavity can form a conduit with an open inlet and an open outlet. The intervening cavity can include a fill material. The fill material can impart rigidity to the conduit body when the conduit body is in the second state.

In another aspect, disclosed herein is an assembly for the formation of a conduit within the body of a subject. The assembly includes an obturator adapted to provide rigidity to the assembly; an expandable member positioned at an outer surface of the obturator and adapted to expand radially; and a conduit device. The conduit device includes a central cavity that seats the expandable member; an outer body having at least a first layer and an opposable second layer, wherein the first and second layers are manufactured from a biocompatible and malleable material that permits safe positioning within the body of the subject; and an enclosed intervening cavity positioned between the first and second layers. The first surface of the first layer forms a first perimeter of the intervening cavity and a second surface of second layer forms a second perimeter of the intervening cavity. The intervening cavity includes a fill material that can interlock the first layer with the second layer. The outer body is configured to transition from a first state to a second state by the application of a suction force to the intervening cavity wherein the outer body is less rigid in the first state compared to the second state.

The conduit device can further include a retention member adapted to retain the outer body in the second state after removal of the suction force. The first surface of the first layer of the outer body can further include at least one feature configured to interlock with the second surface of the second layer. The at least one feature of the first surface of the first layer can impart rigidity to the outer body when the outer body is in the second state. The fill material can form a more rigid mass when the outer body is in the second state than when the outer body is in the first state. A volume of the intervening cavity can be greater when the outer body is in the first state than when the outer body is in the second state. The first layer and the second layer can be separated by a distance, wherein the distance is greater when the outer body is in the first state than when it is in the second state. The central cavity of the device can form a conduit with an open inlet and an open outlet.

In another aspect, disclosed is a method of creating a surgical conduit within a body of a subject. The method includes identifying a target tissue using a radiographic modality; advancing an assembly through a skin incision and onto the target tissue. The assembly includes an obturator adapted to provide rigidity to the assembly; an expandable member positioned at an outer surface of the obturator and adapted to expand radially; a conduit member having a central cavity that seats the expandable member. The conduit member further includes an outer body having at least a first layer and an opposable second layer. The first and second layers are manufactured from a biocompatible and malleable material that permits safe positioning within the body of the subject. The conduit member also includes an enclosed intervening cavity positioned between the first and second layers. The first surface of the first layer forms a first perimeter of the intervening cavity and a second surface of second layer forms a second perimeter of the intervening cavity. The intervening cavity includes a fill material that can interlock the first layer with the second layer. The outer body is configured to transition from a first state to a second state by the application of a suction force to the intervening cavity and the outer body is less rigid in the first state compared to the second state. The method also includes expanding the expandable member and forcibly increasing the outer diameter of the conduit member of the assembly; applying a suction force to the intervening cavity of the outer body and transitioning the outer body into the second state; removing the expandable member and the obturator from the central cavity of the conduit member; and accessing the target tissue through the central cavity of the conduit member.

The conduit member can further include a retention member adapted to retain the outer body in the second state after removal of the suction force. The assembly can be advanced onto the target tissue under manual guidance or under stereotactic guidance. The method can further include using a sheath to encase an outer aspect of the conduit member. The method can further include passing a needle to the target tissue and subsequently passing the assembly along the needle to the target tissue. Expanding the expandable member can determine the diameter of the surgical conduit created. The surgical conduit to the target tissue can be linear or curvilinear. The method can further include attaching the conduit member to a first segment of a mount attached at a second segment to a defined anatomical position relative to the target tissue. The central cavity can further include a port configured to resist centripetal tissue pressure. The central cavity can further include a port configured to focus light and increase light intensity at the target tissue.

BRIEF DESCRIPTION OF THE DRAWINGS

FIGS. 2A-2D illustrate an embodiment of an expandable element in an expanded configuration;
FIGS. 3A-3B illustrate a cross-sectional, schematic view showing an embodiment of locking elements of the expandable element;
FIGS. 4A-4B illustrate a cross-sectional, schematic view showing an embodiment of locking elements of the expandable element;
FIGS. 5A-5B illustrate a cross-sectional, schematic view showing an embodiment of fill material of the expandable element;
FIGS. 6A-6B illustrate schematic view showing an embodiment of locking elements on the outer wall of the expandable element;
FIGS. 9A-9C illustrate another embodiment of an expandable element.

DETAILED DESCRIPTION

Figure 1A:
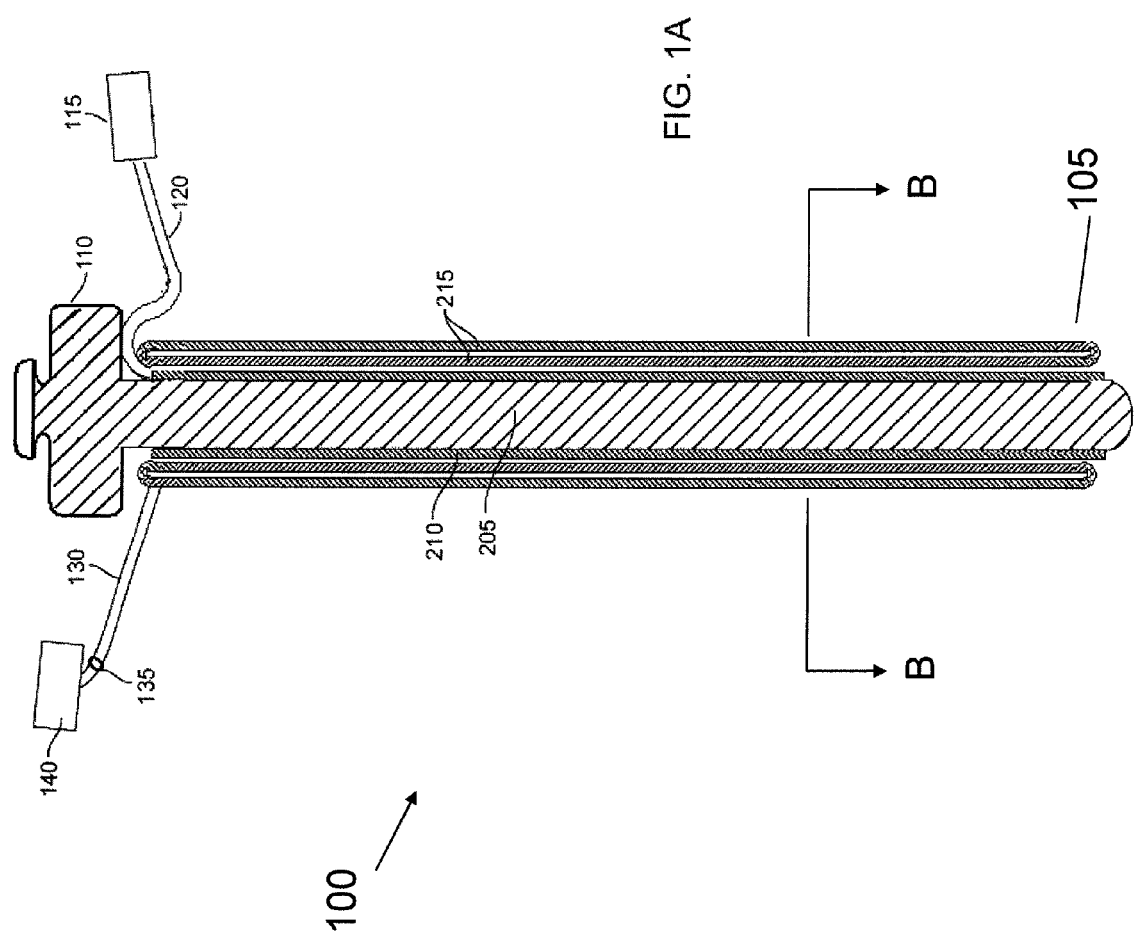
FIG. 1A illustrates a perspective view of an embodiment of the system.

In order to promote an understanding of the principals of the disclosure, reference is made to the drawings and the embodiments illustrated therein. Nevertheless, it will be understood that the drawings are illustrative and no limitation of the scope of the invention is thereby intended. Any such alterations and further modifications in the illustrated embodiments, and any such further applications of the principles of the invention as illustrated herein are contemplated as would normally occur to one of ordinary skill in the art.

Disclosed is a system and method for a variable-shaped, expandable device that may be used inside the body of a human or animal subject. In general, the system includes an expandable element that is expanded from a first configuration to a second configuration. When in the second configuration, the element can then be reversibly transitioned from a malleable to a rigid or semi-rigid state by applying suction within an internal cavity of the element.

The device can be positioned in a first, malleable state into a region of the body of a subject, shaped to a desired second configuration, and then transitioned to a rigid or semi-rigid state. Preferably, but not necessarily, the device can be placed while configured in a first size or shape and then expanded into a second size or shape prior to transitioning into the rigid or semi-rigid state, wherein, in the preferred embodiment, the first size or shape is smaller than the second size or shape. In alternative embodiments and methods of use, it is contemplated that the device can be used on the internal or exterior aspect of a tissue segments inside the body in order to repair, augment, replace, expand or contract a tissue segment. For example, the internal/external aspect of the gastro-intestinal tract may be reinforced or partitioned by the device. The device may be used to seal a breach, perforation or defect within the tract or, for example, to partition a portion of the stomach or intestine (or form a space occupying mass within the stomach/intestinal tract) for weight loss. The urological, reproductive, respiratory systems, and the like may be similarly repaired or partitioned using the device. In additional embodiment, the device can be used within the internal or external aspect of the vascular system (i.e., blood vessels, etc.) or lymphatic system to repair, augment, replace, or re-shape (expand or contract) a segment of the system or to form an alternative conduit for the fluids carried therein. The device can be also used within the orthopedic system to abut and splint bones and joints, to aid, repair, and/or replace segments of ligaments (such as a synthetic ligament) or muscle structures, and as a component of an orthopedic implant or device. As such it should be appreciated that the devices described herein can be inserted into body cavities or can be used to create new tissue passages in the body. The device can be made of absorbable or non-absorbable materials.

In an embodiment, the device may be used as a retractor that can be used to create, enlarge and retract a tissue passage for the insertion of instruments for minimally-invasive surgery. While a device embodiment is illustrated for use in this application, it is understood that that the system may be alternatively used in a variety of other uses and methods within the body cavity of a subject.

In an embodiment, the device can perform the function of a tissue retractor. The device can be configured to form a conduit and the conduit can be used in multiple different ways. The conduit may be cylindrical or of a non-cylindrical geometric shape. Use of the conduit as a surgical corridor will be described below. The system allows procedures, such as tumor resection, to be performed with conventional or specialized instruments through a relatively small corridor. The system can be used in the field of fiber optic surgery, including endoscopy, arthroscopy, laparoscopy, etc. which involve looking into and operating within a limited space with a fiber optic light and/or camera. While the devices described herein may be used in any region of the body in which minimally-invasive access is desirable, they are well adapted for use in brain and spine surgery.

FIG. 1A illustrates a sectional side view of an embodiment of a system. The system 100 generally includes a proximal, hand-held component 110 and a distal, working end 105. The initial small diameter of the working end 105 allows for a relatively small incision to be made through which the device may be inserted. The expansion of the working end 105 to a larger diameter can stretch the tissue surrounding the working end 105. Upon deflation of the working end 105 to the smaller diameter, the tissue can return to its initial un-stretched condition.

Figure 1B:
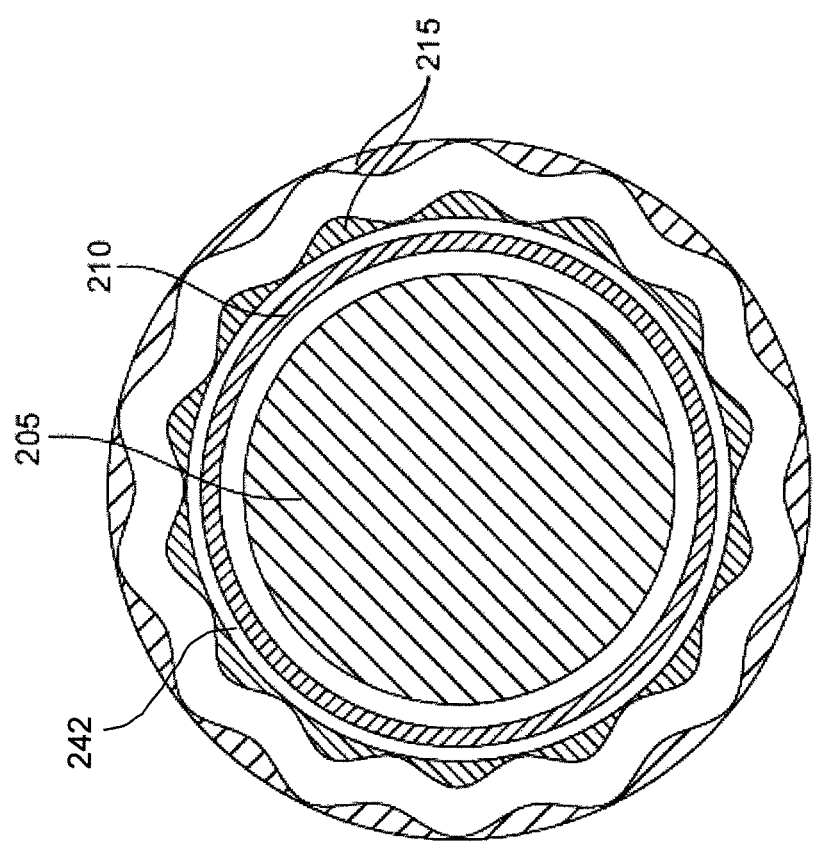
FIG. 1B illustrates a cross-sectional view of the embodiment of FIG. 1A taken along line B-B.

As best shown in FIGS. 1A and 1B, the device can include a central obturator 205 surrounded by an inner expandable element 210, which is in turn surrounded by or extending through a central channel 242 of an outer expandable element 215. The inner expandable element 210 can be similar to a traditional balloon that upon inflation with a fluid, including a liquid or gas, can expand radially outwardly (i.e. centrifugally) such that the inner expandable element 210 presses against the outer expandable element 215.

Figure 10:
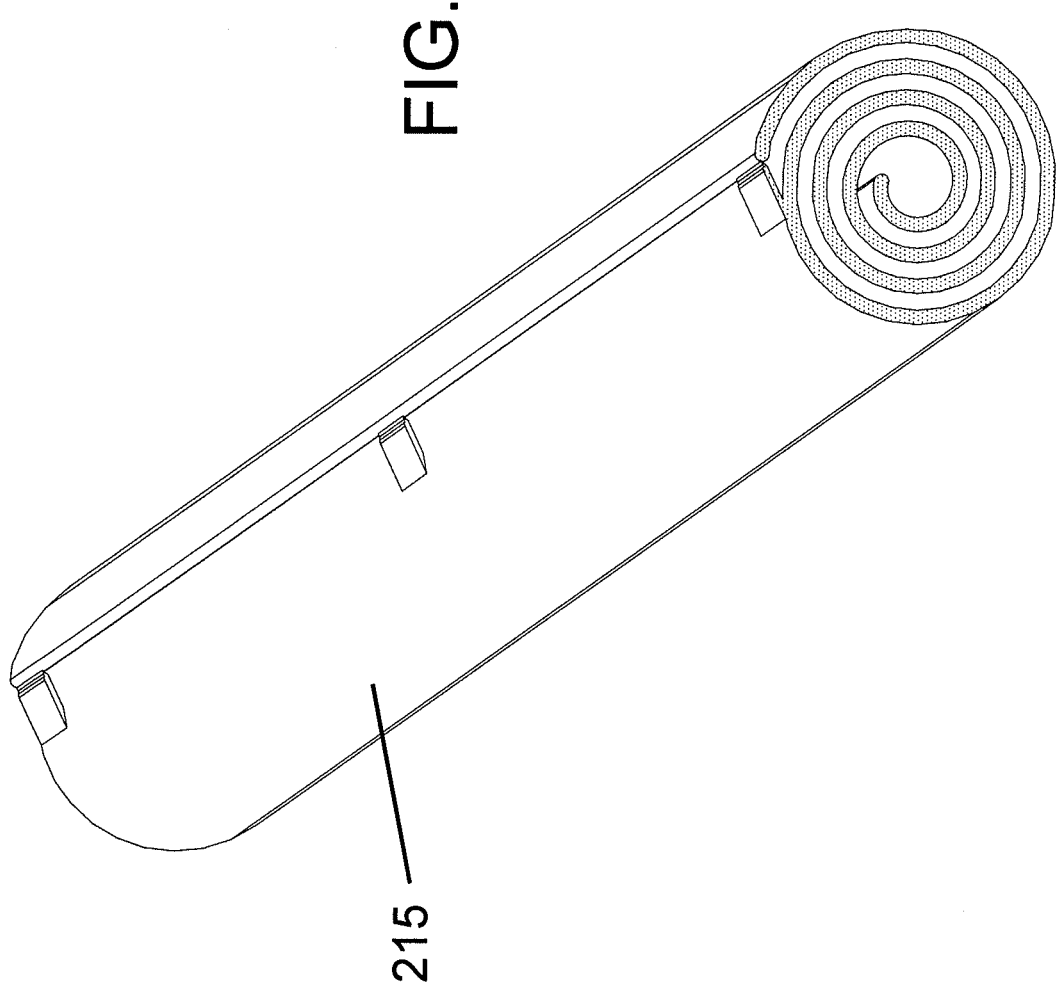
FIG. 10 illustrates another embodiment of an expandable element.

As best shown in FIG. 2A, the outer expandable element 215 can have a tubular shape such that it can expand outwardly forming a substantially cylindrical configuration having a central channel 242. It should be appreciated however, that the size and shape of both the inner and outer expandable elements 210, 215 can vary. The inner and outer expandable elements 210, 215 can be round, eccentric, oval, conical, wedge-shaped, U-shaped, curved, angled, or another shape that may be desirable to optimize a particular application. While the outer expandable element 215 is depicted as a cylindrical tube, it should be appreciated that the element 215 may be alternatively made in a sheet-like configuration, wherein the sheet is rolled into a cylindrical configuration and can be unfurled (see FIG. 10), in manner similar to rolling a sheet-like carpet into a cylindrical structure (or rolling a cigar from a sheet of tobacco). Similarly, it should be appreciated that although the working end 105 of the system is shown as having a generally circular cross-sectional shape that other shapes are considered herein, for example, an elliptical or oval-shaped working end 105. In addition, the shape of cross-sections obtained at different regions, levels, or planes of the implant may differ from one another.

The inner and outer expandable elements 210, 215 can be formed of a soft, compliant material and preferably have no sharp edges which might injure tissue. The material of the expandable elements 210, 215, to an extent desired, can conform to the tissue confines. One or more of the expandable elements 210, 215 can be manufactured as is known in the art of elastomeric or non-elastomeric materials. Materials can include, but are not limited to thin-walled polymers, Silastic elastomer, silicone, latex, PVC, Kevlar or Mylar, nylon, or other fiber to prevent puncturing and to provide structural shape and support as desired, suitable thermoplastic materials, soft polyvinyl chloride, nylon, polypropylene, polyethylene, fluoropolymers, urethane, copolymers of polyvinyl chloride and vinyl acetate, metallic alloys, shape memory alloys, and mixtures of nanotube fibers (such as carbon nanotubes, etc.), carbon fibers materials, polyvinyl chloride and synthetic rubber. The thermoplastic material may be further composed of a composite, such as a woven nylon material with a protective coating of urethane or vinyl.

As mentioned, inflation of the inner expandable element 210 expands its outer diameter (i.e. radial expansion) such that it presses against the walls of the central channel 242 and expands the outer expandable element 215. Thus, the outer expandable element 215 need not be coupled directly to a gas and/or fluid driven expansion source in order to achieve radial expansion. Expansion of the inner and outer expandable elements 210, 215 can enlarge the overall diameter of the working end 105. In an embodiment, the outer diameter of the working end 105 can be about 10 mm. After the inner, expandable element 210 is inflated, the working end 105 can have an outer diameter of about 30 mm. It should be appreciated, however, that other diameter dimensions are also contemplated.

The material used to fill the expandable element 210 can vary including, but not limited to air, dextrose water, normal saline, $CO_2$, $NO_2$ and the like. Generally, physiologically safe fluids are used such that if the fluid should accidentally escape into the body, no ill effects are observed. The pressure in the expandable element 210 and also expandable element 215 can be monitored and regulated such that the force exerted by the device is sufficient to cause expansion and maintained at a level safe to prevent tissue damage without over expansion or tissue necrosis. The system 100 can include a regulator to control the force of expansion and/or a pressure sensor. The expanding portion is less bulky and more compact, and the pressure it applies at the tissue edges can stop bleeding of divided tissues.

FIGS. 2A-2D illustrate an embodiment of the outer expandable element 215 in an expanded configuration. When the outer expandable element 215 is expanded inside the body, it retracts tissue. As mentioned above, the outer expandable element 215 can have a generally donut or tubular shape such that it has an outer wall 220 and an inner wall 225, and an elongate, central channel 242 through which the obturator 205 and inner expandable element 210 can extend. The outer and inner walls 220, 225 of the outer expandable element 215 are sealed such that they create a hollow, inner cavity or chamber 240. The chamber 240 can be connected by conduit 130 to a vacuum source 140 controllable by an actuator 135, such as a valve or other actuator means (see FIG. 1A). Exposure of the inner chamber 240 between the outer and inner walls 220, 225 to the vacuum source 140 applies suction and pulls the outer and inner walls 220, 225 towards one another effectively eliminating the inner chamber 240 (see FIGS. 2C-2D), as will be discussed in more detail below. The chamber 240 can be a closed space in order to hold the suction force generated by the vacuum device. Each of the expandable elements 210, 215 can have controllable inflow-outflow portals that can be a simple tube or conduit 120, 130 with an on-off valve attached or another suitable structure.

The outer expandable element 215 can reversibly transition from a malleable element to an element having a rigid or semi-rigid configuration. The outer wall 220 and the inner wall 225 can each have complementary locking elements 230, 235 that project into the inner chamber 240. Applying suction to evacuate the inner chamber 240 can cause the locking elements 230, 235 to come into contact, reversibly interlock, and impart rigidity to the once-malleable walls of the outer expandable element 215. The connection between the locking elements 230, 235 can prevent the inner and outer walls from slipping past one another such that the outer expandable element 215 can act as a rigid retractor and maintain the tissue corridor opening. The malleable nature of the outer expandable element 215 (prior to vacuum evacuation of inner chamber 240) provides for a wide variety of shapes to which it can conform. After vacuum evacuation of inner chamber 240, element 215 can transition to the semi-rigid or rigid configuration and maintain the shape to which it was shaped.

Figure 7A:
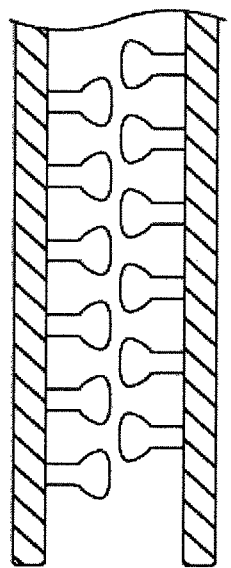
FIGS. 7A-7B illustrate a cross-sectional, schematic view showing an embodiment of locking elements of the expandable element.
Figure 7B:
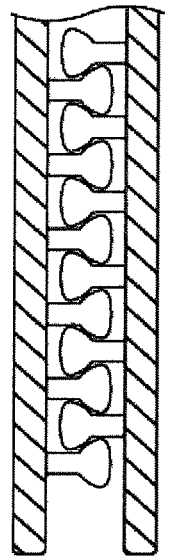

As mentioned, the locking elements 230, 235 can be generally complementary, reciprocal cut-out features such that as they approach one another they can join into a friction engagement. The locking elements 230, 235 can have rounded geometry (FIG. 3A-3B) or the locking elements 230, 235 can have more square geometry (FIGS. 4A-4B). The locking elements 230, 235 can also have irregular shapes that interlock with one another by virtue of certain surface structures such as flanges or lips or ridges as shown in FIG. 7A.

The locking elements 230, 235 can also form a variety of surface patterns on the inner surface of the outer wall 220 (See FIGS. 6A-6B). The locking elements 230, 235 can form regular or irregular patterns, such as, for example, a series of raised mounds or elongated ridges. One set of locking elements can be indentations and the other set of locking elements can be complementary three-dimensional structures that can project into the indentations. Further, the holding power of the locking elements 230, 235 can be further enhanced by coating the inner surface of the walls 220, 225 with materials having adhesive or magnetic properties.

It should be appreciated that the locking elements need not be surface structures on the walls themselves. FIGS. 5A-5B show an embodiment in which a fill material 245 is implanted within the inner chamber 240 of the outer expandable element 215. The fill material 245 can vary. The fill material 245 can include, but is not limited to, particles, beads, granules, flakes or a gel containing fill material 245. The fill material 245 can be a variety of shapes, materials and quantities such that fill material 245 is free to move or flow within the inner chamber 240 to obtain a desired shape or contour and retain the shape or contour when the inner chamber 240 is evacuated. Such materials may include, for example, abrasives, sand, glass particles, "liquid metal" (see product information at www.liquidmetal.com/index/default.asp) and the like. FIG. 5A shows the fill material 245 somewhat sparsely distributed throughout the inner chamber 240 such that the element 215 is malleable and the fill material 245 and the walls are free to move. Applying suction and shrinking the inner chamber 240 can cause the walls to approach one another resulting in the fill material 245 becoming more densely packed and "hardened" (FIG. 5B). This rigid configuration allows otherwise malleable walls 220, 225 to maintain the tissue corridor. In an embodiment, the fill material can be placed within cavity 240 and the surface of opposable walls 220, 225 has no complementary locking elements (see FIG. 5). Alternatively, fill material can be added to cavity 240 containing complimentary locking elements of walls 220, 225 wherein the fill material can enhance conduit wall rigidity after the device has been exposed to suction.

In an embodiment, the outer expandable element 215 can have proximal tabs 310 near a proximal end (see FIGS. 9A-9C). After insertion of the working end 205 of the device towards a target tissue, the tabs 310 can be folded over such that the tabs 310 contact an external tissue surface of the work space surrounding the corridor. The tabs 310 can become rigid along with the rest of the outer expandable element 215 such that they cover the tissue surface and prevent injury of adjacent tissues near the external surface and entry to the corridor. For example, in the case of brain surgery the tabs 310 can protect the surface of the brain surrounding the corridor formed by the device (320 in FIG. 9C).

Methods of Use

It should be appreciated that any number of procedures can be performed using the systems described herein, including minimally-invasive procedures on an internal target tissue, such as the internal/external aspect of the blood vessels, the internal/external aspect of the gastro-intestinal tract, the internal/external aspect of the respiratory tract, the internal/external aspect of the urological and/or reproductive organs, the resection of mass lesions and tumors, and the like.

A method of use will now be described. The procedure is preferably, but not necessarily, performed under image guidance. The imaging technique may involve any applicable imaging modality that can be used to identify the target within the body of a subject. These techniques include, but are not limited to, plain X-ray radiography, fluoroscopy, CT, MRI, PET, SPECT scan, radio-isotope imaging techniques and the like. Further, the imaging technique(s) may be combined with stereotactic guidance methods to further guide the trajectory of device placement. Stereotactic guidance of surgical procedures is well known in the art and varied guidance systems are commercially available to accomplish that purpose.

In an embodiment, a target region identified within the body of a subject is selected. The target is identified on an imaging modality and a trajectory to the target is selected. The distal, working end of 105 of the system 100 can be inserted through a small skin incision and advanced along the selected tissue trajectory to the target region. While system 100 may be placed using "free-hand" (i.e., unaided manual guidance) positioning, it is contemplated that the system 100 can be guided to the target using iterative imaging under an image modality or through the use of a system adapted to guide manipulation of tissues. The use of a frame or frameless based stereotactic guidance systems can be used. Devices such the "Brain Lab" system are commercially available stereotactic guidance systems. The Brain Lab systems are illustrated at: www.brainlab.com/scripts/website_english.asp and the web site contents are hereby incorporated by reference. Other embodiments of the technique are illustrated in "Frameless Stereotaxy of the Brain" by McInerney and Roberts in *Mt Sinai J Med*. September; 67(4):300-10 and "Devices for Targeting the needle" by Barbre in *Neurosurg Clin N. Am.* 2009 April; 20(2): 187-91, which are each hereby incorporated by reference in their entirety.

The obturator 205 can provide structural rigidity to the inner and outer expandable elements 210, 215 during insertion, which can each be deflated during insertion such that they are tightly disposed against the obturator 205 (FIG. 1A). An additional sheath may be used to encase the outer aspect of element 215 and to further reduce friction and hasten device passage through tissues.

In an alternative embodiment, a needle or guide wire can be inserted through a small skin incision and advanced along the selected tissue trajectory to the region of the target. It is contemplated that the needle or guide wire can be guided to the target using iterative imaging under an image modality or through the use of stereotactic guidance and the like. In this embodiment, central obturator 205 can contain an internal bore (not shown) that is adapted to accept a needle or guide wire therethrough. The internal bore can be central or eccentric in position. The needle or guide wire may be malleable or rigid. The portion of the needle or guide wire that is outside the subject's body can then be passed through the internal bore of central obturator 205. The distal, working end of 105 of the system 100 can be inserted through the small skin incision and advanced along the needle or guide wire to the region of the target.

Upon reaching the target tissue site, the inner expandable element 210 can be inflated and radially expanded outward (i.e. centrifugally) by slowly applying pressure through conduit 120 from source 115. The inner expandable element 210 can extend through the central channel 242 of the tubular-shaped such that outer expandable element 215 of the inner expandable element 210 presses against the inner wall 225 of the outer expandable element 215 and thereby expands the outer expandable element 215 simultaneously. Thus, the outer expandable element 215 need not be coupled directly to a pressure source to achieve radial expansion. The expansion of the inner and outer expandable elements 210, 215 creates a tissue corridor from an external portion of the body, through the selected tissue trajectory, and onto the target tissue site. The diameter of the corridor created can vary and can be determined by the degree to which the inner expandable element 210 is expanded. Prior to vacuum evacuation of the internal space 240, the malleable nature of the outer expandable element 215 provides for a wide variety of shapes to which it can conform and ultimately maintain once it is transitioned into the rigid configuration.

Figure 8B:
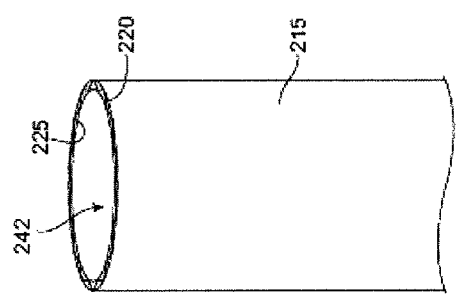
FIGS. 8A-8D illustrate schematic views of an embodiment of the working end of the system.

The outer and inner walls 220, 225 of the outer expandable element 215 can still remain generally separated from one another upon radial expansion (see FIG. 8B). Suction can then be applied to evacuate the inner chamber 240 by vacuum source 140 through conduit 130 by switch actuator 135 causing the outer wall 220 and inner wall 225 to approach one another (see FIG. 8C). As the outer wall 220 and inner wall 225 approach one another so too do the locking elements 230, 235 (or fill material 245, if applicable) such that the locking elements 230, 235 reversibly interlock. The connection between the locking elements 230, 235 or the compaction of the fill material 245 prevents the inner and outer walls from slipping past one another and imparts a rigid or semi-rigid contour to the outer expandable element 215 such that it can maintain the tissue corridor.

Figure 8D:
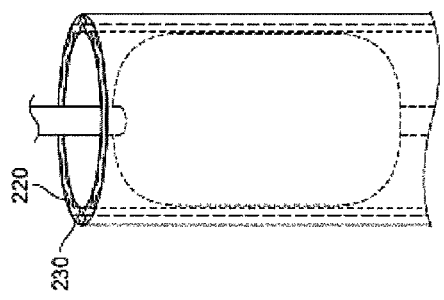
Figure 8A:
Figure 8C:
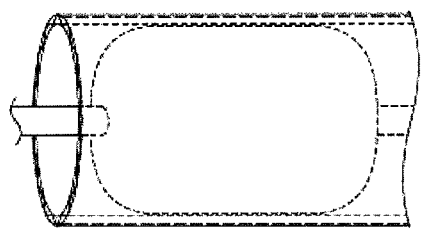

The inner expandable element 215 can then be deflated, and withdrawn along with the central obturator 110/205 (see FIGS. 1A, 8D). Having transitioned into the more rigid (or completely rigid) state, the inner expandable element 215 can maintain the created tissue corridor for the passage of a variety of surgical instruments to the targeted tissue site. It is understood that the conduit or corridor thus formed need not be cylindrical or of uniform diameter or shape. The conduit or corridor can be of any applicable geometry and can vary in geometry and size within different areas and cross-sections of the corridor. Further, the corridor can be linear or curvilinear. Curvilinear conduits or corridors are especially advantageous in permitting access to a target tissue while navigating around important anatomical structures that may reside within a linear trajectory between the skin incision and the target tissue.

Once the conduit or corridor is established within expanded element 215, the device can be hand-held and retained at the target tissue for the desired period of time. Alternatively, a segment of element 215 that rests outside of the body cavity of the subject (i.e., outside of the skin) may be configured to be attached to a first segment of a mount, where the mount is in turn attached at a second segment to a defined anatomical position relative to the target tissue. In this way, the mount can retain the device at the target site for a desired period of time. A first segment of the mount, for example, can attach to a proximal segment of the element 215 (i.e., a segment of the retractor device that is outside of the body cavity) while a second segment of the mount can anchor to the operating table, an instrument in the operating suite, to a different segment of the patient, or the like. In another embodiment, the mount can attach to a distal segment (i.e., a segment of the retractor device that is inside of the body cavity) of the device and anchor it to the target tissue directly or to another internal body tissue. As an example of the latter embodiment, the target tissue can be a bony element wherein the mount is a screw, pin, clip, or abutment surface (and the like) that couples the distal segment of the device to bone tissue at or adjacent to the target site.

Instruments can be passed through the established corridor within expanded element 215 and a procedure can be performed as desired. Conventional or specialized surgical instruments can be used through the retractor corridor. In addition, suction, irrigation, light sources, microscopes and other magnification instruments, endoscopes and other surgical implements can be used to access and/or manipulate the target though the expanded element 215. In this way, the system 100 permits the minimally-invasive passage of the retractor system into the body of a subject, expansion of the malleable portion of the system to a desired configuration, and then transition of the malleable portion to a semi-rigid or rigid state that is adapted to retain the shape of the established corridor. The target tissue can then be manipulated as desired through the corridor.

The device can be positioned in a first malleable state into a region of the body of a subject, shaped to the desired configuration, and then transitioned to a second rigid or semi-rigid state. Preferably, but not necessarily, the device can be placed in a first size or shape and then transfigured into a second size or shape prior to transitioning into the rigid or semi-rigid state, wherein the first size or shape is smaller than the second size or shape. The device can be configured to form a conduit and the conduit can be used in multiple different ways.

If the device is used in tissues with substantial resistance to dilatation, it may be difficult for element 215 to maintain the shape of the conduit, e.g. after transition to the rigid or semi-rigid state, because of the high centripetal force exerted by the surrounding tissues. In this situation, it is contemplated that an additional port, such as for example a metallic cylinder with an internal bore, may be placed through space 242 of element 215 to maintain the conduit in the expanded and rigid or semi-rigid configuration. The port placed within space 242 of expanded element 215 may serve additional purposes. For example, the port can be configured to accept a light source to further illuminate the contents within space 242. Further, the internal bore of the port can be coated and/or configured in such a manner as to focus and/or diffract the light of a light source and increase the intensity of the light available at the target tissue. Likewise, the port can be configured to decrease the glare of light reflected off of the internal bore itself while simultaneously increasing the light intensity at the distal end of the port.

Use of the conduit as a surgical retractor has been described above. In alternative methods of use, it is contemplated that the device can be used on the internal or exterior aspect of a substantially cylindrical segment of tissue to repair, augment, replace, expand or contract a tissue segment. By way of example, the device can be used within the internal or external aspect of the vascular system (i.e., blood vessels, etc.), and the internal/external aspect of the gastro-intestinal, urological, reproductive, and respiratory systems. The device can be also used within the musculoskeletal system to abut and splint bone and joints, to function in a semi-rigid state to aid, repair, and/or replace segments of ligaments (such as a synthetic ligament) or muscle structures, and as a component of an orthopedic implant or device. Orthopedic devices include implants adapted to attach to bone, cartilage and/or ligaments and bear at least a portion of the structural load transmitted through the skeletal system.

The device can be made of any known bio-compatible materials that are known or will be known in the future. Materials currently considered acceptable for biological implantation are known and include, but are not limited to, elastomers (such as rubber and the like), a cloth (woven or other-wise), a fiber (natural, semi or synthetic or man-made or combinations thereof) a mesh, various plastics, resins, ceramics, metals, metallic alloys, and the like. The device can be made of biologically absorbable materials or non-absorbable materials. The device may be radio-lucent or radiopaque.

Any components may be also coated/made with growth factors to further tissue incorporation. For example, in orthopedic applications, the device may include osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous in growth surface (such as titanium wire mesh, plasma-sprayed titanium, tantalum, porous CoCr, and the like), provided with a bioactive coating, and/or helical rosette carbon nanotubes (or other nanotube-based coating). The system or any of its components can also be entirely or partially made of a shape memory material or other deformable material.

It is further contemplated that the system may be used therapeutically in the treatment of tumors or other conditions. In that use, the system may be employed to deliver biomodulation factors to the target region in order to regulate (promote, inhibit and the like) the growth of neighboring tissues. These factors include growth factors, inhibitors of growth factors, radioactive agents, chemotherapeutic agents, genetic vectors (for gene therapy) or other agents adapted to affect the growth, development and/or differentiation of tissues.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method of creating a surgical conduit within a body of a subject, comprising:
   identifying a target tissue using a radiographic modality;
   advancing an assembly through a skin incision and onto the target tissue, the assembly comprising:
      an obturator adapted to provide rigidity to the assembly;
      an expandable member positioned at an outer surface of the obturator and adapted to expand radially; and
      a conduit member comprising a central cavity that seats the expandable member, the conduit member further comprising:
         an outer body having at least a first layer and an opposable second layer, wherein the first and second layers are manufactured from a biocompatible and malleable material that permits safe positioning within the body of the subject; and
         an enclosed intervening cavity positioned between the first and second layers, wherein a first surface of the first layer forms a first perimeter of the intervening cavity, wherein a second surface of second layer forms a second perimeter of the intervening cavity and wherein the intervening cavity comprises a fill material that can interlock the first layer with the second layer;
   expanding the expandable member and forcibly increasing an outer diameter of the conduit member of the assembly;
   applying a suction force to the intervening cavity of the outer body and transitioning the outer body from a first state to a second state, the outer body being less rigid in the first state compared to the second state;
   removing the expandable member and the obturator from the central cavity of the conduit member; and
   accessing the target tissue through the central cavity of the conduit member.

2. The method as in claim 1, further comprising retaining the outer body in the second state after removal of the suction force via a retention member of the conduit member.

3. A method as in claim 1, wherein the act of advancing the assembly onto the target tissue comprises advancement thereof under manual guidance.

4. A method as in claim 1, wherein the act of advancing the assembly onto the target tissue comprises advancement thereof under stereotactic guidance.

5. A method as in claim 1, further comprising using a sheath to encase an outer aspect of the conduit member.

6. A method as in claim 1, further comprising passing a needle to the target tissue and subsequently passing the assembly along the needle to the target tissue.

7. A method as in claim 1, wherein expanding the expandable member determines the diameter of the surgical conduit created.

8. A method as in claim 1, wherein the surgical conduit to the target tissue is linear.

9. A method as in claim 1, wherein the surgical conduit to the target tissue is curvilinear.

10. A method as in claim 1, further comprising attaching the conduit member to a first segment of a mount attached at a second segment to a defined anatomical position relative to the target tissue.

11. A method as in claim 1, wherein the central cavity further comprises a port configured to resist centripetal tissue pressure.

12. A method as in claim 1, wherein the central cavity further comprises a port configured to focus light and increase light intensity at the target tissue.

13. A method to access a target tissue within a body of a subject, comprising:
   identifying said target tissue using an imagining technique;
   advancing a surgical conduit assembly through a skin entry site and onto said target tissue, said conduit assembly comprising a perimeter wall at least partially enclosing an internal channel, and an internal expandable member at least partially contained within said internal channel, said perimeter wall comprised of an inner wall member, an outer wall member and an intervening cavity therebetween;
   transitioning said perimeter wall from a first configuration to a second configuration in which each of said inner wall member, said outer wall member, and said internal channel are of a larger diameter than when said perimeter wall is in said first configuration;
   applying a suction force within said intervening cavity, said act of suction application immobilizes said inner wall member relative to said outer wall member; and
   accessing said target tissue at least partially through said internal channel.

14. The method of claim 13, wherein at least one feature of said inner wall member interlocks with a complimentary feature of said outer wall member when said perimeter wall is in said second configuration.

15. The method of claim 13, wherein said internal channel comprises an opening at each of a proximal and distal end.

16. The method of claim 13, further comprising placing a fill material within said intervening cavity.

17. The method of claim 16, wherein said fill material imparts rigidity to said surgical conduit assembly after application of said suction force.

18. The method of claim 13, further comprising retaining said surgical conduit assembly in said second configuration after removal of said suction force.

19. A method to access a target within a brain of a subject, comprising:
- identifying said target using an imaging modality;
- creating a tissue corridor within said brain by advancing an instrument assembly from an entry point of an outer surface of said brain to said target, said instrument assembly comprising:
  - an elongated member having a proximal end and a distal end; and
  - a conduit extending from a proximal end to a distal end along a longitudinal axis, and comprises an internal bore that extends there between, said internal bore being sized to at least partially seat said elongated member therein;
- positioning said instrument assembly with: a) said distal end of said elongated member at said target; b) said proximal end of said conduit being outside of said brain; c) a distal segment of an outer perimeter surface of said conduit abutting at least a segment of said tissue corridor; and d) a proximal segment of said outer perimeter surface of said conduit comprising at least one projection extending outwardly and away at a distance greater than said outer perimeter surface, the at least one projection abutting said outer surface of said brain and at least partially surrounding said surface entry point;
- removing said elongated member from said internal bore; and
- accessing said target through said internal bore of said conduit; and
  - wherein said conduit retains said tissue corridor from decreasing in diameter after removal of said elongated member.

20. A method as in claim 19, wherein a diameter of said conduit may be varied.

21. A method as in claim 19, wherein an outer diameter of said conduit is configured to increase in size.

22. A method as in claim 21, wherein a conduit of greater outer diameter comprises a internal bore of greater diameter.

23. A method as in claim 19, wherein at least a segment of said instrument assembly is manufactured from a plastic material.

24. A method as in claim 19, wherein at least a segment of said instrument assembly is manufactured from a metallic material.

25. A method as in claim 19, wherein said conduit is configured to provide a linear trajectory to said target.

26. A method as in claim 19, wherein said conduit provides a curvilinear trajectory to said target.

27. A method for positioning a device within a subject, comprising:
- identifying target tissue using an imagining technique;
- advancing a conduit assembly through a skin entry site and onto said target tissue, said conduit assembly comprising an outer expandable member at least partially enclosing an internal channel, and an internal expandable member at least partially contained within said internal channel;
- expanding said internal expandable member of said conduit assembly to generate an outwardly directed force;
- transitioning an outer perimeter wall of said outer expandable member from a first configuration to a second configuration, said outer perimeter wall being malleable, non-rigid and having a first diameter in said first configuration, and said outer perimeter wall being non-malleable, rigid, and having a second diameter greater than said first diameter in said second configuration;
- retaining said outer perimeter wall of said outer expandable member in said second configuration;
- removing said internal expandable member from said internal channel; and
- accessing said target tissue at least partially through said internal channel;
- wherein said act of retaining said outer perimeter wall in said second configuration is performed at least in part by a retention member of said conduit assembly, and said act of retaining persists after removal of said outwardly directed force.

28. The method of claim 27, wherein said act of advancing said conduit assembly through said skin entry site and onto said target tissue comprises manually advancing said assembly therethrough.

29. The method of claim 27, wherein said act of advancing said conduit assembly through said skin entry site and onto said target tissue comprises using at least one device for stereotactic guidance.

30. The method of claim 27, wherein said act of advancing said conduit assembly through said skin entry site and onto said target tissue comprises passing a needle to said target tissue and subsequently passing said conduit assembly along said needle to said target tissue.

31. The method of claim 27, wherein said act of expanding said internal expandable member determines a diameter of said internal channel.

32. The method of claim 27, further comprising attaching said conduit assembly to a first segment of a mount, a second segment of said mount attached to a defined anatomical position relative to said target tissue.

33. The method of claim 27, further comprising resisting centripetal tissue pressure via a port located on said internal channel.

34. The method of claim 27, further comprising focusing light and increasing light intensity at said target tissue via a port located on said internal channel.

35. A method for formation of a conduit onto a target tissue within a body of a subject, comprising:
- identifying said target tissue using an imagining technique;
- advancing a surgical conduit assembly through a skin entry site and onto said target tissue, said conduit assembly comprising a perimeter wall at least partially enclosing an internal channel, and an internal expandable member at least partially contained within said internal channel, said perimeter wall comprised of an inner wall member, an outer wall member and an intervening cavity therebetween;
- transitioning said perimeter wall from a first configuration to a second configuration in which each of said inner wall member, said outer wall member, and said internal channel are of a larger diameter than when said perimeter wall is in said first configuration;
- applying a suction force to said intervening cavity, said suction force retaining said perimeter wall in said second configuration; and
- accessing said target tissue at least partially through said internal channel;
- wherein a volume of said intervening cavity of said perimeter wall is greater when said perimeter wall is in said first configuration than when in said second configuration.

36. The method of claim 35, further comprising interlocking at least one feature of said inner wall member with a complimentary feature of said outer wall member when said perimeter wall is in said second configuration.

37. The method of claim 35, wherein said internal channel comprises an open inlet and an open outlet.

38. The method of claim 35, further comprising placing a fill material within said intervening cavity.

39. The method of claim 38, wherein said fill material imparts rigidity to said surgical conduit assembly when in said second configuration.

40. The method of claim 35, further comprising retaining said surgical conduit assembly in said second configuration after removal of said suction force.

* * * * *